United States Patent [19]

Vinson

[11] Patent Number: 4,722,843

[45] Date of Patent: Feb. 2, 1988

[54] MOISTURIZING NUTRITIVE AND HEALING SKIN CREAM

[76] Inventor: William L. Vinson, 6145 Vine St., Philadelphia, Pa. 19139

[21] Appl. No.: 689,159

[22] Filed: Jan. 7, 1985

[51] Int. Cl.$^4$ .............................................. A61K 35/78
[52] U.S. Cl. .................................. 424/195.1; 514/847
[58] Field of Search ..................... 424/195.1; 514/777, 514/847

[56] References Cited

U.S. PATENT DOCUMENTS 4,297,374 10/1981 Wess .................................... 514/777

FOREIGN PATENT DOCUMENTS 2388555 12/1978 France ................................. 514/777

Primary Examiner—J. R. Brown
Assistant Examiner—John W. Rollins, Jr.
Attorney, Agent, or Firm—Susan B. Evans

[57] ABSTRACT

A skin moisturizing, nutritive, and healing cream is produced by blending a predominant quantity of juices from an avocado, cucumber, lady's mantle or burdock, red clover, and white willow and the remainder being lemon juice and anhydrous lanolin wherein the lanolin being the major portion of the remainder. The ingredients are blended to a creamy texture and the cream is massaged into the skin by hand.

8 Claims, No Drawings

MOISTURIZING NUTRITIVE AND HEALING SKIN CREAM

BACKGROUND OF THE INVENTION

This invention relates to a novel skin cream composition which is substantially greaseless in application and which cleanses, moisturizes, nourishes, and heals the skin.

Various compositions of cleansing and/or moisturizing cream and lotion preparations are known in the prior art that include fruits, vegetables, and the juices thereof. French Pat. No. 2,388,555 discloses a cosmetic product having a lanolin base and using fruits and vegetables such as lemon, cucumber, carrot, orange and juices thereof. U.S. Pat. No. 4,297,374 discloses a skin moisturizing and cleansing cream of a blended mixture of which the major portion being a fresh fruit such as bananas or avocados and the remainder being baking powder, orange juice, and vegetable shortening.

No prior art was found that discloses the composition of the present invention.

SUMMARY OF THE INVENTION

The present invention provides an improved skin cleansing and moisturizing cream or lotion which cleanses the skin of dirt, removes dry skin, nourishes the skin, and simultaneously moistens the skin; all of this is done without causing irritation of the skin by excessive rubbing or scrubbing or causing irritation to the eyes if applied close thereto.

The skin moisturizing, nutritive, and healing cream comprises by volume of mixture a predominant amount of the juices of avocado, cucumber, lady's mantle or burdock, red clover, and weeping willow and the remainder of lemon juice and anhydrous lanolin wherein said lanolin being the major portion of the remainder.

The present invention also comprehends a method of cleansing and moisturizing the skin comprising thoroughly washing and rinsing the skin with water, massaging the above mentioned cream into the skin, wiping the excess cream from the skin, and applying cold water to the skin to lock the cream into the pores of the skin.

DETAILED DESCRIPTION OF THE INVENTION

The skin moisturizing, nourishing, and cleansing cream composition according to the present invention comprises a base of lanolin which is preferrably anhydrous lanolin. It is present in an amount of from about 15% to about 70% by volume. Lanolin is the best matrix available to keep the other ingredients sealed to the skin so that the skin is moisturized, healed, nourished, and cleansed. In other words, the natural action of the lanolin along with the permitting of the natural action of the other ingredients unexpectedly provides superb outer enhancement of the skin.

The active ingredients of the skin moisturizing, nourishing, and cleansing cream composition of this invention include an effective amount of weeping willow extract which brings comfort to burning and itching skin. The weeping willow will clear the skin of pimples and discolorations. While weeping willow should be present in the composition in the amount of from about 3% to about 6%.

The weeping willow extract is prepared by splitting about 1 part by weight of weeping willow twigs, sticks or branches and placing the split weeping willow twigs, sticks, or branches in about 20 parts by weight of water. The twigs are boiled in water until a solution of weeping willow juices in water, having the approximate color of tea, is formed. The twigs are then removed from the solution which comprises the weeping willow extract. A suitable weeping willow extract has been formed by boiling about three ounces of split, chopped weeping willow twigs in about one-half gallon of water for about ½ hour.

Lady's mantle or burdock is a herb that is used as an ingredient in the composition of this invention. A tea (or extract) of this ingredient is prepared in a similar manner as the weeping willow by boiling in water. This ingredient imparts antiseptic characteristics to the composition which helps to kill infection causing microorganisms. Red clover is also a herb which is an ingredient in the instant invention which is prepared as a tea (or extract) as the other herbs are prepared. Red clover is a natural healing ingredient which soothes and makes the skin feel refreshed.

Lady's mantle or burdock and red clover are used in an amount of from about 3% to about 20% of the composition. The preferred range is about 4% to about 16%.

The juices of an avocado and a cucumber are also ingredients of this composition that impart healing and nutritive as well as moisturizing characteristics to the composition. Those juices should be added in the amount of from about 3% to about 20%, preferrably from about 4% to about 16%.

The juice of a lemon, an ingredient, imparts many characteristics to the composition. Lemons are natural bleaching agents and natural preservatives. They also help the other ingredients to be blended together. In other words, they act as a medium into which the other ingredients readily dissolve or are dispersed.

The natural fruits, vegetables, and herbs of this invention provide the skin with all of the natural vitamin and minerals required to maintain a healthy skin. It is also important to remember that a person's eating habits play a vital role in promoting good health. In order for a person to have truly healthy looking and beautiful skin, the person must eat daily a nutritious and well balanced diet, get proper amount of rest, and exercise the body to keep the muscles toned up.

The skin moisturizing and cleansing cream of the present invention will be understood with reference to the following example which is intended to exemplify the composition, the method of its preparation, and the method of its use.

EXAMPLE

| Ingredient | Amt. Fl. Oz. | % by Volume |
| --- | --- | --- |
| Anhydrous Lanolin | 16 | 64 |
| Avocado | 1 | 4 |
| Cucumber | 1 | 4 |
| Lady's Mantle or Burdock | 1 | 4 |
| Red Clover | 1 | 4 |
| White Willow | 1 | 4 |
| Lemon | 4 | 16 |
|  | 25 | 100 |

The base of the moisturizing and cleansing cream composition in accordance with this example is prepared by placing the anhydrous lanolin in a blender and beating to a foamy consistency for about 30–45 minutes. The cucumber and avocado juices are boiled in a vessel for several minutes at a temperature of 80° C. and then blended into the foamy lanolin one at a time until thoroughly mixed. The herbs, i.e. Lady's mantle, red clover, and weeping willow, are individually extracted (or made into a tea) in hot water at a temperature of about 180° C. for several minutes (until the proper color is reached) and then added one at a time to the foamy lanolin until thoroughly mixed. The lemon juice is blended into the lanolin mixture for about 15 minutes. The end product is similar in consistency to a face cream. Trace amount of a fragrance was added to enhance the aroma of the cream.

The mixture was used by several people for one week as a night cream and under makeup. They first thoroughly washed and rinsed their skin with a mild soap and water. The skin included the face, neck, elbows, arms, hands and legs and feet. Small amounts of the cream were then massaged into the skin. After the massaging, the skin was then lightly rinsed with cold water to close the pores of the skin, thus sealing in the cream to the skin. The skin was then either wiped lightly with dry facial tissues or a dry wash cloth. The subjects, depending on the skin areas on which the cream was applied, found the cream to provide for the skin to have a texture which was smooth and soft to the touch with a desirable tautness to the skin, to moisturize areas of the skin whch were dry and flaky such as after bathing or showering, and to heal and remove bruises, abrasions, marks, and discolorations.

I claim:

1. A skin moisturizing, nutritive and healing cream comprising by volume of a mixture of the juice of 1-6 parts of avocado, juice of 1-6 parts of cucumber, 1-6 parts of lady's mantel or burdock aqueous extract, 1-6 parts of red clover aqueous extract and 1-6 parts of weeping willow aqueous extract, 4-8 parts of lemon juice and 16-32 parts of anhydrous lanolin.

2. The skin cream according to claim 1 wherein said avocado is 1 part by volume, cucumber is 1 part by volume, lady's mantle or burdock is 1 part by volume, red clover is 1 part by volume, weeping willow is 1 part by volume, lemon is 4 parts by volume and anhydrous lanolin is 16 parts by volume.

3. The skin cream according to claim 1 wherein said avocado is 4 parts by volume, cucumber is 4 parts by volume, lady's mantle is 4 parts by volume, red clover is 4 parts by volume, weeping willow is 4 parts by volume, lemon is 16 parts by volume and anhydrous lanolin is 32 parts by volume.

4. A method of making a given volume of skin moisturizing, nutritive and healing cream comprising placing in a mixing receptacle to provide said volume, 1-6 parts of avocado juice, 1-6 parts of cucumber juice, 1-6 of lady's mantel or burdock aqueous extract, 1-6 parts of red clover aqueous extract, 1-6 parts of weeping willow aqueous extract, 4-8 parts of lemon juice and 16-32 parts of anhydrous lanolin, and mixing said ingredients in said receptacle to a creamy texture.

5. The method according to claim 4 wherein the lanolin is placed in a blender and beat for 15-45 minutes until it is a light foamy consistency, the cucumber, avocado and lemon are juiced and strained and the pure juices are boiled at a temperature of about 100° C., the juices are then blended one at a time into the lanolin and then beat for a period of 10-30 minutes a piece; the herbs are dissolved in hot water, heated to a temperature of about 180° C., and blended into the lanolin mixture one at a time and beat for a period of 10-30 minutes a piece, a fragrance is then added during the final 5-10 minutes of blending of the mixture.

6. The method according to claim 5 wherein the vegetables and fruits are blended into the lanolin for a period of 15 minutes each, the herbs are blended into the lanolin for a period of 15 minutes each and a fragrance is blended into the lanolin for a period of 10 minutes.

7. The method according to claim 6 wherein said avocado juice is 1-6 parts by volume, cucumber juice is 1-6 parts by volume, lady's mantle or burdock juice is 1-6 parts by volume, red clover juice is 1-6 parts by volume, weeping willow juice is 1-6 parts by volume, lemon juice is 4-16 parts by volume and anhydrous lanolin is 16-32 parts by volume.

8. The method according to claim 6 wherein said avocado juice is 1 part by volume, cucumber juice is 1 part by volume, lady's mantle or burdock juice is 1 part by volume, red clover juice is 1 part by volume, weeping willow juice is 1 part by volume, lemon juice is 4 parts by volume and anhydrous lanolin is 16 parts by volume.

* * * * *